(12) United States Patent
Yadav et al.

(10) Patent No.: US 6,391,044 B1
(45) Date of Patent: May 21, 2002

(54) VASCULAR FILTER SYSTEM

(75) Inventors: Jay S. Yadav, South Russell, OH (US); Gregg S. Sutton, Maple Grove, MN (US); Amy Raatikka, Minneapolis, MN (US); Thomas Borillo, Plymouth, MN (US)

(73) Assignee: Angioguard, Inc., Plymouth, MN (US)

(*) Notice: Subject to any disclaimer, the term of this patent is extended or adjusted under 35 U.S.C. 154(b) by 0 days.

(21) Appl. No.: 09/249,377

(22) Filed: Feb. 12, 1999

Related U.S. Application Data

(63) Continuation-in-part of application No. 09/155,753, filed on Oct. 2, 1998, and a continuation-in-part of application No. 08/794,011, filed on Feb. 3, 1997, now abandoned.
(60) Provisional application No. 60/101,226, filed on Sep. 21, 1998, provisional application No. 60/101,227, filed on Sep. 21, 1998, provisional application No. 60/101,228, filed on Sep. 21, 1998, and provisional application No. 60/101,171, filed on Sep. 21, 1998.

(51) Int. Cl.$^7$ ............................................... A61M 29/00
(52) U.S. Cl. ....................................................... 606/200
(58) Field of Search ............................ 606/200, 1, 159, 606/198

(56) References Cited

U.S. PATENT DOCUMENTS

| | | |
|---|---|---|
| 3,952,747 A | 4/1976 | Kimmel, Jr. |
| 4,349,029 A | 9/1982 | Mott |
| 4,425,908 A | 1/1984 | Simon |
| 4,619,246 A | 10/1986 | Molgaard-Nielsen et al. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |

(List continued on next page.)

FOREIGN PATENT DOCUMENTS

| | | |
|---|---|---|
| EP | 737450 | 10/1996 |
| GB | 2020557 | 11/1979 |
| WO | WO 96/01591 | 1/1996 |

OTHER PUBLICATIONS

Eichelter, et al., "Prophylaxis of Pulmonary Embolism," *Archives of Surgery*, vol. 97, Aug. 1968, pp. 348 et seq.

Greenfield, et al., "A New Intercaval Filter Permitting Continued Flow and Resolution of Emboli," *Surgery*, vol. 73, No. 4, pp. 599–606.

Cragg et al., "A New Percutaneous Vena Cava Filter", *AJR*, 141, Sep. 1983, pp. 601–604.

Cragg et al., "Nonsurgical Placement of Arterial Endoprosthesis: A New Technique Using Nitinol Wire", *AJR*, Apr. 1983, pp. 261–263.

Lund et al., "Long–term Patency of the Ductus Arteriosus After Balloon Dilatation: An Experimental Study" *AJR*, Sep. 1983, pp 772.

M.H. Wholey et al., "PTA and Stents in the Treatment of Extracanial Circulation", *Journal of Invasive Cardiology*, vol. 8, Suppl. E, 1996, pp. 25E–30E.

*Primary Examiner*—Michael H. Thaler
(74) *Attorney, Agent, or Firm*—Cohen, Liebowitz & Latman, P.C.; William H. Dippert; Paul A. Coletti

(57) ABSTRACT

A removable vascular filter system for blocking micro- and macro-emboli while allowing the continued perfusion of blood comprises a filter membrane positioned on a guidewire, wherein a free end of the membrane sits tightly against the guidewire when the filter membrane is in a collapsed state and wherein the filter has a means for deploying the filter membrane to assume a position substantially normal to the longitudinal axis of the guidewire. The filter membrane is comprised of a fine mesh material which has a pore size capable of blocking emboli while allowing continued blood flow, a preferred embodiment of which comprises regularly spaced, laser-formed holes.

34 Claims, 19 Drawing Sheets

U.S. PATENT DOCUMENTS

| | | |
|---|---|---|
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,842,579 A | 6/1989 | Shiber |
| 4,873,978 A | 10/1989 | Ginsburg |
| 4,921,484 A | 5/1990 | Hillstead |
| 4,926,858 A | 5/1990 | Gifford, III et al. |
| 4,969,891 A | 11/1990 | Gewertz |
| 5,011,488 A | 4/1991 | Ginsburg |
| 5,053,008 A | 10/1991 | Bajaj |
| 5,092,839 A | 3/1992 | Kipperman |
| 5,108,419 A | 4/1992 | Reger et al. |
| 5,152,777 A | 10/1992 | Goldberg et al. |
| 5,190,546 A | 3/1993 | Jervis |
| 5,201,757 A * | 4/1993 | Heyn et al. ................. 606/198 |
| 5,329,942 A | 7/1994 | Gunther et al. |
| 5,421,832 A | 6/1995 | Lefebvre |
| 5,549,626 A | 8/1996 | Miller et al. |
| 5,662,671 A | 9/1997 | Barbut et al. |
| 5,695,519 A | 12/1997 | Summers et al. |
| 5,769,816 A | 6/1998 | Barbut et al. |
| 5,779,716 A | 7/1998 | Cano et al. |
| 5,814,064 A | 9/1998 | Daniel et al. |
| 5,827,324 A | 10/1998 | Cassell et al. |
| 5,848,964 A | 12/1998 | Samuels |

* cited by examiner

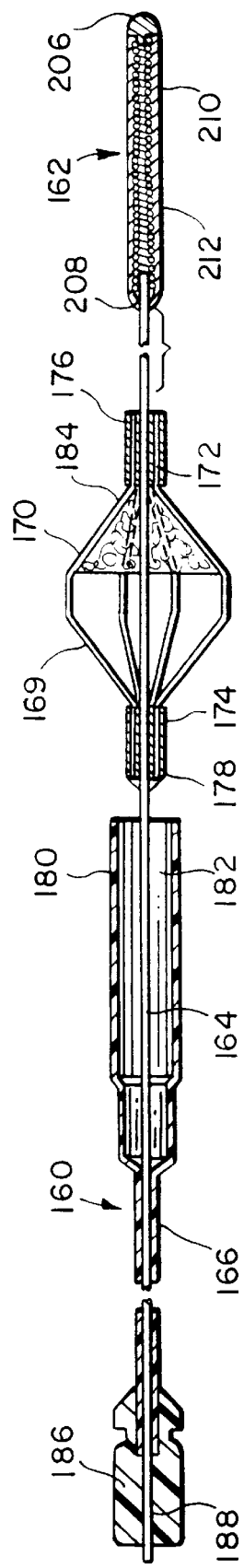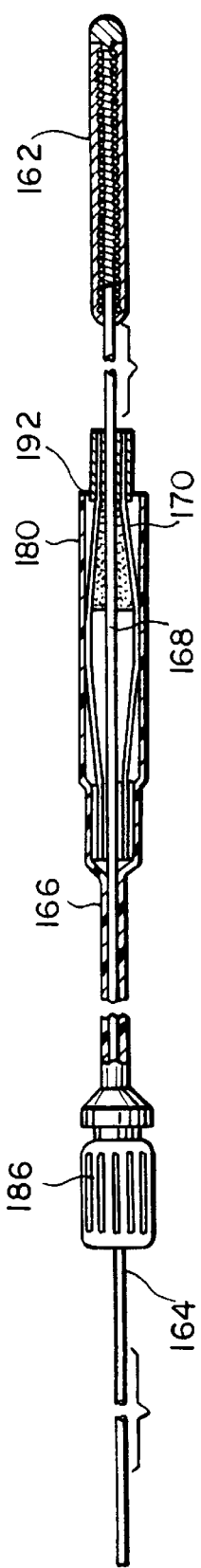

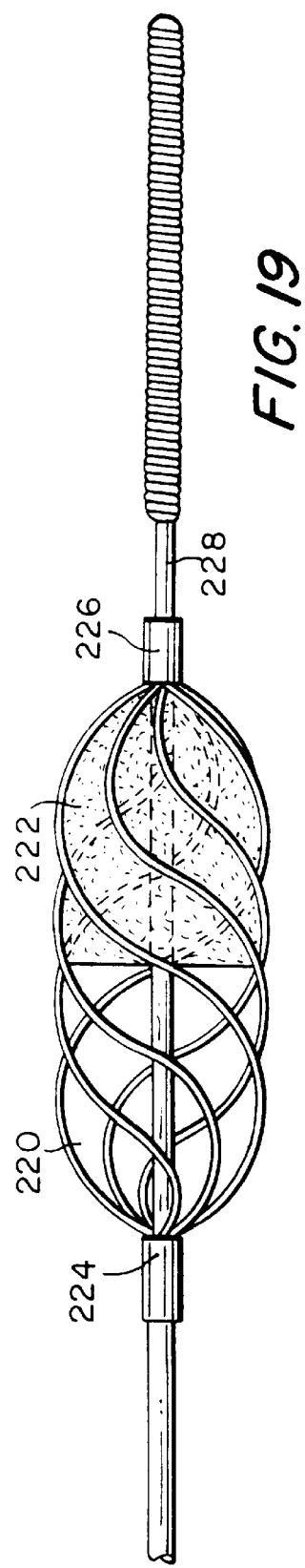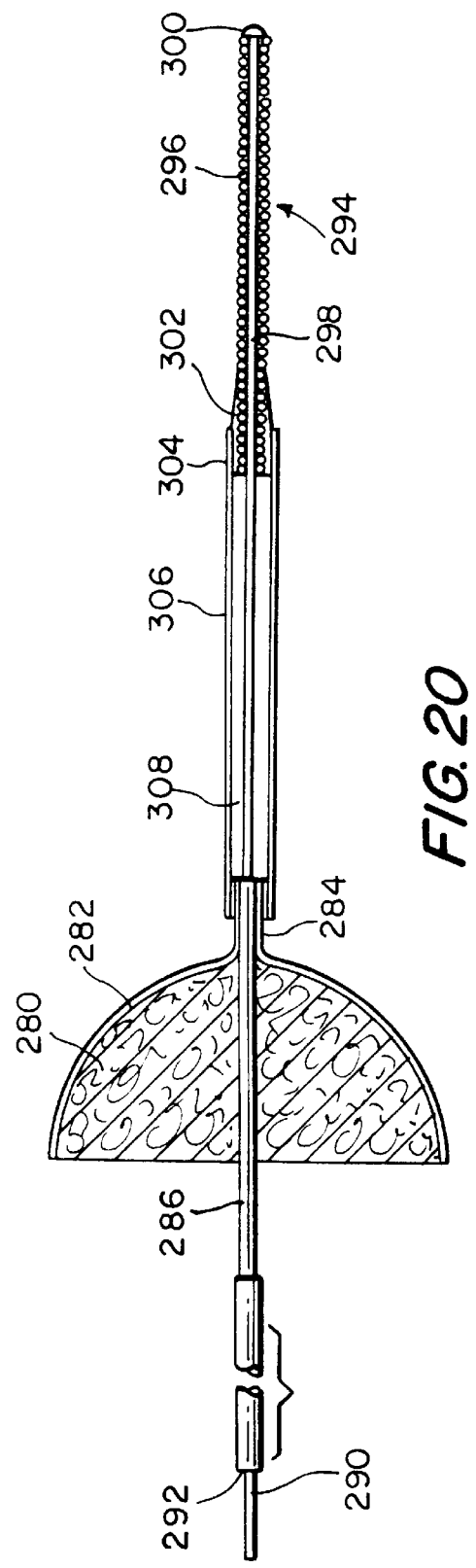

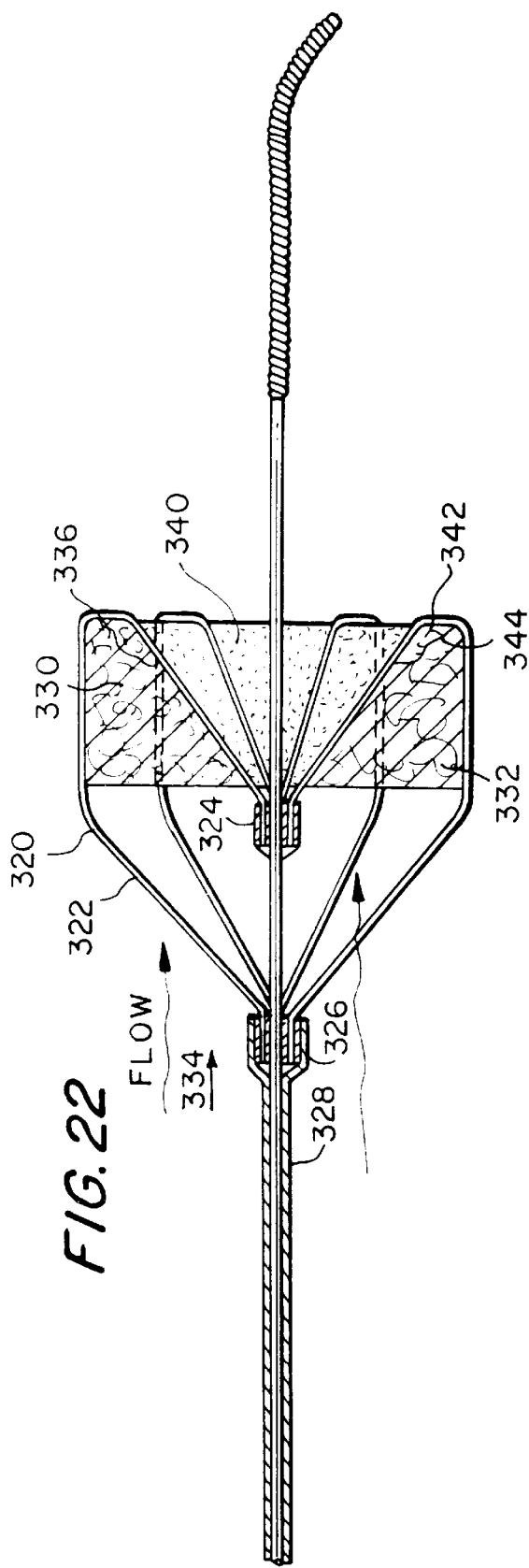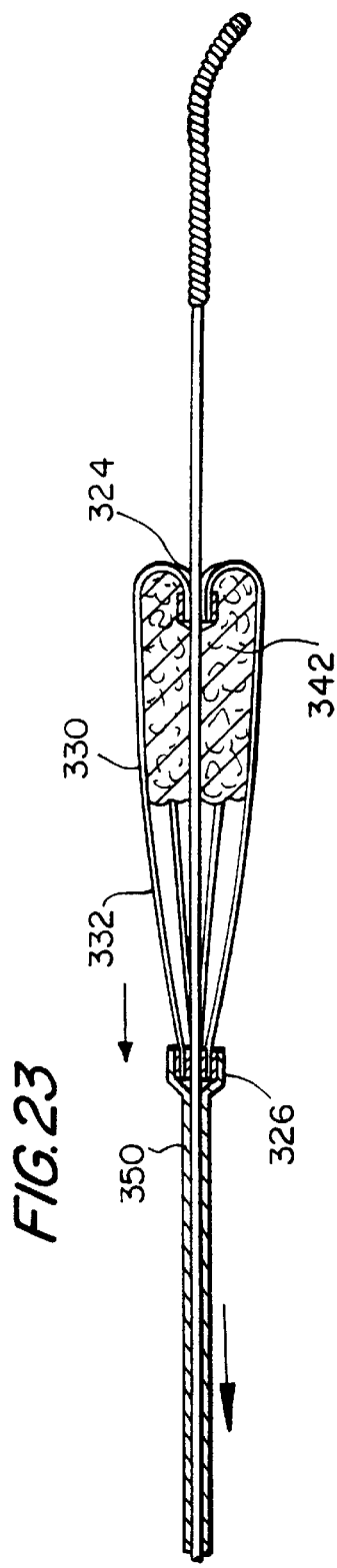

VASCULAR FILTER SYSTEM

CROSS-REFERENCE TO RELATED APPLICATIONS

This patent application is a continuation-in-part of U.S. patent application Ser. No. 08/794,011, filed Feb. 3, 1997 now abandoned, pending U.S. patent application Ser. No. 09/155,753, filed Oct. 2, 1998, U.S. provisional patent application Ser. No. 60/101,226, filed Sep. 21, 1998, U.S. provisional patent application Ser. No. 60/101,227, filed Sep. 21, 1998, U.S. provisional patent application Ser. No. 60/101,228, filed Sep. 21, 1998, and U.S. provisional patent application Ser. No. 60/101,171, filed Sep. 21, 1998 all of which are incorporated herein by reference.

FIELD OF THE INVENTION

The present invention relates to the treatment of vascular disease by either surgery or percutaneous angioplasty and stenting. More particularly, the invention relates to a system that reduces macro- and micro-embolization during the treatment of vascular stenosis.

BACKGROUND OF THE INVENTION

A variety of surgical and non-surgical angioplasty procedures have been developed for removing obstructions from blood vessels. Balloon angioplasty utilizes a balloon-tipped catheter which may be inserted within a stenosed region of the blood vessel. By inflation of the balloon, the stenosed region is dilated. Surgery involves either removing the plaque from the artery or attaching a graft to the artery so as to bypass the obstructing plaque. Other techniques, such as atherectomy, have also been proposed. In atherectomy, a rotating blade is used to shave plaque from an arterial wall.

One problem common with all of these techniques is the accidental release of portions of the plaque or thrombus, resulting in emboli which can lodge elsewhere in the vascular system. Such emboli are, of course, extremely dangerous to the patient, frequently causing severe impairment of the distal circulatory bed. Depending upon the vessel being treated, this may result in a stroke or myocardial infarction or limb ischemia.

Vascular filters or embolism traps for implantation into the vena cava of a patient are well known, being illustrated by, for example, U.S. Pat. Nos. 4,727,873 and 4,688,553. Additionally, there is a substantial amount of medical literature describing various designs of vascular filters and reporting the results of the clinical and experimented use thereof. See, for example, the article by Eichelter & Schenk entitled "Prophylaxis of Pulmonary Embolism," Archives of Surgery, Vol. 97, August 1968, pp. 348 et seq. See, also, the article by Greenfield, et al., entitled "A New Intracaval Filter Permitting Continued Flow and Resolution of Emboli", Surgery, Vol. 73, No. 4, pp. 599–606 (1973).

Vascular filters are used, often during a postoperative period, when there is a perceived risk of a patient encountering a pulmonary embolus resulting from clots generated at the surgical site or the like. As a typical use of vascular filters, the filter is mounted in the vena cava to catch large emboli passing from the surgical site to the lungs.

The vascular filters of the prior art are usually permanently implanted in the venous system of the patient, so that even after the need for the filter has abated, the filter remains in place for the lifetime of the patient, absent surgical removal. U.S. Pat. No. 3,952,747 describes a stainless steel filtering device which is permanently implanted transvenously within the inferior vena cava. The filtering device is intended to treat recurrent pulmonary embolism. U.S. Pat. No. 4,873,978 describes a catheter device comprising a catheter body having a strainer mounted at it distal end. The strainer is shiftable between an opened configuration where it extends substantially across the blood vessel to entrap passing emboli, and a closed configuration where it retains the captured emboli during removal of the catheter. A mechanism actuable at the proximate end of the catheter body allows selective opening and closing of the strainer. Typically, the strainer is a collapsible cone having an apex attached to a wire running from the distal end to the proximate end of the catheter body.

Permanent implantation is often deemed medically undesirable, but it has been done because vascular filters are implanted in patients primarily in response to potentially life threatening situations. Accordingly, the disadvantages of permanent implantations of a vascular filter are often accepted.

To avoid permanent implantation, it would be highly desirable to provide an apparatus and method for preventing embolization associated with conventional surgery and angioplasty procedures. In particular, it would be desirable to provide a device which could be located within the vascular system to collect and retrieve portions of plaque and thrombus which have dislodged during the surgery or angioplasty procedure.

OBJECT OF THE INVENTION

It is an object of this invention to provide a vascular filter system for reducing macro- and micro-embolization.

It is also an object of the invention to provide a vascular filter system which is readily removable from the vascular system, or elsewhere, of a patient when the filter is no longer needed.

It is a further object of the invention to provide a vascular filter system having a configuration which does not require hooks to penetrate and grip the blood vessel walls, so that the implantation results in less blood vessel injury.

It is a yet further object of the invention to provide a vascular filter system of very low profile which is part of a guidewire and can be used in small vessels.

These and other objects of the invention will become more apparent from the description below.

SUMMARY OF THE INVENTION

The present invention generally relates to a vascular filter system useful in the surgical or interventional treatment of vascular disease, in particular, a novel percutaneous angioplasty and stenting system useful, for example, in the treatment of carotid stenoses. Macro- and micro-embolization occurs during percutaneous procedures such as angioplasty, which increases the risk of a minor or major stroke. The system of the present invention for reducing macro- and micro-embolization is very useful in helping to prevent the risk of stroke. However, this system would also be useful in any angioplasty or surgical procedure where embolization is a risk.

The vascular filter system of the present invention will decrease embolism while allowing brain, or other distal tissue, perfusion. The filters are incorporated into a guidewire which is used for the entire procedure from crossing a lesion to deploying a stent. In one embodiment the filter consists of a thin membrane attached to the guidewire and supported by fine metal spines. Attachment of the filter membrane to the guidewire allows expansion of the filter membrane with a firm fit inside the artery. The attachment also allows for collapse of the filter membrane at the end of the procedure so it fits tightly against the guidewire and can be withdrawn through the guide catheter. In another embodiment, the filter membrane rests upon or is attached to a basket-like structure, at least one end of which is attached to the guidewire. The filter membrane has a pore size such that blood flow is not impeded when the filter membrane is expanded but micro- and macro-emboli are blocked. Expansion of the filter membrane is aided by the forward flow of blood against the filter. The filter design results in a very low profile so that the initial crossing of the lesion is minimally traumatic. Also, the small diameter and small profile facilitate use of the device in small or larger arteries with minimal or no obstruction of blood flow.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which:

FIG. 14 is a lateral, partly cross-sectional view of one embodiment of the invention with the filter membrane in an open position;

FIG. 15 is a lateral, partly cross-sectional view of the embodiment of the invention in FIG. 14 with the sheath closed;

FIG. 19 is a lateral, cross-sectional view of an alternative basket structure for the embodiment of FIG. 14 FIG. 20 is a lateral, partly cross-sectional view of another embodiment of the invention;

FIG. 22 is a schematic, partially cross-sectional view of another embodiment of the invention where the distal section of the filter basket is inverted; and FIG. 23 is a schematic, partially cross-sectional view of the embodiment shown in FIG. 22 where the filter basket is collapsed.

DETAILED DESCRIPTION OF THE INVENTION

The present invention relates to a vascular filter system for use in percutaneous angioplasty and stenting and provides for the prevention of distal embolism during endovascular procedures. Further, the filter system of the invention allows for distal perfusion while preventing embolization.

The system comprises a thin, perforated filter membrane which is capable of blocking emboli and which is attached to the distal end of a guidewire. In one embodiment the system uses thin fibers which are moveable and are attached to or encapsulated by the filter membrane to deploy and/or collapse the filter membrane. The invention also contemplates the use of metal spines or inflatable spines attached to the filter membrane to deploy the filter membrane. The fibers or spines can also be attached to a moveable core which is slidable within the guidewire and is used to deploy and collapse the filter membrane.

The filter membrane deploys in an umbrella-like fashion with the unattached edge of the membrane moving upward, i.e., distally, and outward until it is in firm contact with an artery wall. When the filter membrane is deployed, it spans the cross-sectional area of the vessel lumen being treated for a stenosis such as carotid stenosis, or another condition likely to produce emboli.

In another, preferred embodiment of the invention, a thin, flexible, perforated membrane is supported by four or more supports that form a distally extending basket. At least one end of the basket is attached to the guidewire, and the other, slidable end can be moved to cause the membrane to open or close.

Figure 1:
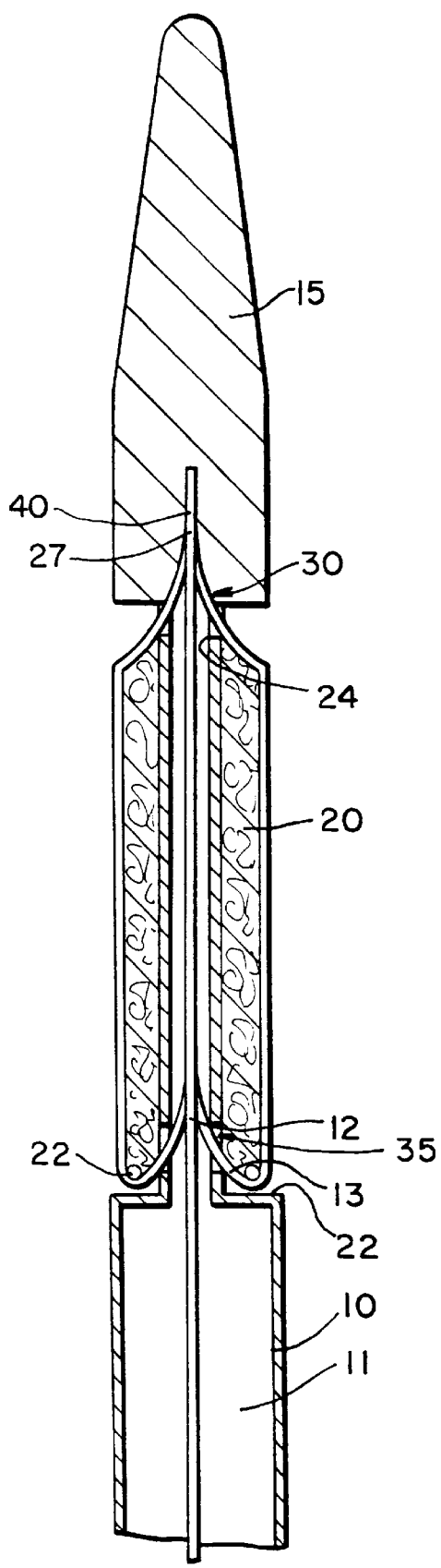
FIG. 1 is a lateral, partly cross-sectional view of the distal end of a guidewire of one embodiment of the invention with the filter membrane in a collapsed position.

The invention can perhaps be better appreciated by reference to the drawings. FIG. 1 illustrates a lateral, cross-sectional view of a distal end of a guidewire 10 with a filter membrane 20 attached thereto. FIG. 1 shows guidewire 10 with a shapeable, tapered soft tip 15 at its extreme distal end which provides flexibility and maneuverability to guidewire 10. The filter membrane in FIG. 1 is in a collapsed position. Filter membrane 20 has a fixed portion 24 which is movably attached to guidewire 10, and filter membrane 20 lies adjacent guidewire 10 proximal to fixed portion 24 when filter membrane 20 is in the collapsed state. A moveable core 40 runs through a center lumen 11 of guidewire 10 and preferably extends distally a short distance beyond fixed portion 24 of filter membrane 20. Deploying wires or fibers 30 are each firmly attached at one end 27 to moveable core 40 distal to fixed portion 21 of filter membrane 20. The deploying fibers are attached at their other ends to filter membrane 20 at attachment points 22.

Collapsing fibers 35 are each firmly attached at one end 12 to the portion of moveable core wire 40 which is interior to filter membrane 20 when it is in the collapsed state. Collapsing fibers 35 are each attached at their other end 13 to filter membrane 20 at attachment points 22. Accordingly, collapsing fibers 35 lie interior to filter membrane 20 when filter membrane 20 is in the collapsed state.

Filter membrane 20 is deployed when the operator pulls moveable core 40 proximally through the interior of guidewire 10. Prior to retraction of moveable core 40, deploying fibers 30 are sufficiently relaxed so as not to create any tension at filter membrane attachment points 22. Upon retraction of moveable core 40, tension is created in deploying fibers 30.

There will preferably be from 2 to 6 each of evenly-spaced deploying fibers 30 and collapsing fibers 35, 3 or 4 being most preferred. The deploying fibers 30 and collapsing fibers 35 can be made of any flexible, medically acceptable material, including stainless steel, nitinol, or another metal or metallic alloy or a non-metallic substance such as graphite or a suitable polymer. In addition, guidewire 10 and moveable core 40 can be made from similar materials, as would be appreciated by those skilled in the art. Typically, guidewire 10 could have an external diameter of from about 0.014 mm to about 0.035 mm, a wall thickness of from about 0.002 mm to about 0.010 mm, and a length of from about 25 cm to about 300 cm. Also, moveable core 40 could have a diameter of from about 0.003 mm to about 0.010 mm and a length of from about 30 cm to about 350 cm.

Figure 2:
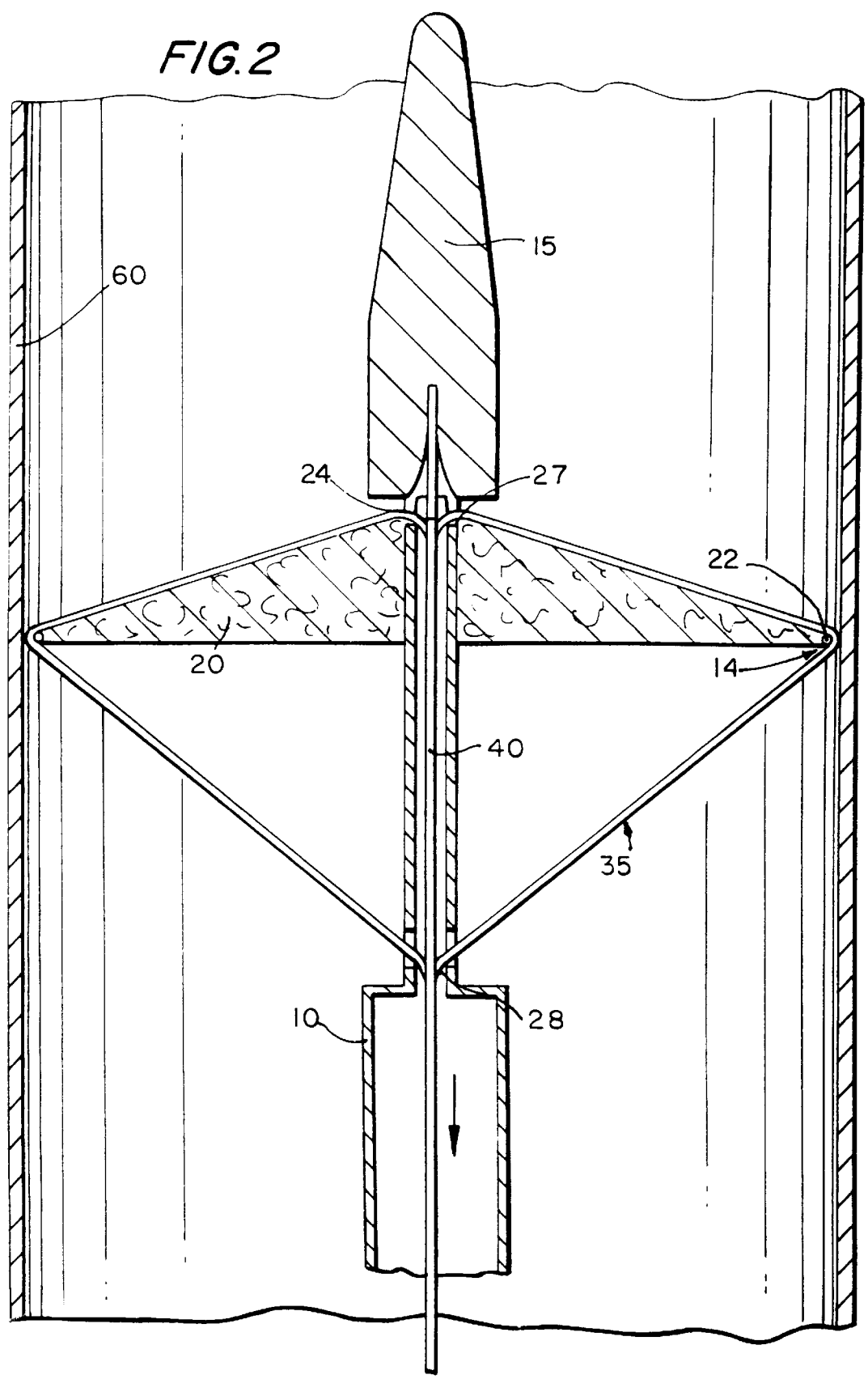
FIG. 2 is a lateral, partly cross-sectional view of the distal end of a guidewire of FIG. 1 with the filter membrane in an expanded, deployed position.

FIG. 2 illustrates the filter device of the invention in a deployed position on the inside of an artery wall 60. Moveable core 40 is in a retracted state, i.e., pulled proximally through the interior of guidewire 10. Tension is created in deploying fibers 30, and filter membrane 20 extends to a deployed position where the outer edge 14 of filter membrane 20 contacts artery wall 60. In this deployed position, collapsing fibers 35 are in a relaxed state and extend from filter membrane attachment points 22 to fixed attachment points 28 on moveable core 40.

The flow of blood in FIG. 2 is toward the distal end of guidewire 10. As such, the force of the flow of blood pushes on deployed filter membrane 20 and helps to maintain filter membrane 20 in the deployed position.

For withdrawal of guidewire 10 and the filter device, filter membrane 20 is collapsed so that it sits tightly against guidewire 10. This is accomplished by extending moveable core 40 distally through guidewire 10, thus relaxing deploying fibers 30 and creating tension in collapsing fibers 35. The tension in collapsing fibers 35 collapses the filter membrane 20, allowing it to fit tightly against guidewire 10 in recess 16 as depicted in FIG. 1.

Figure 3:
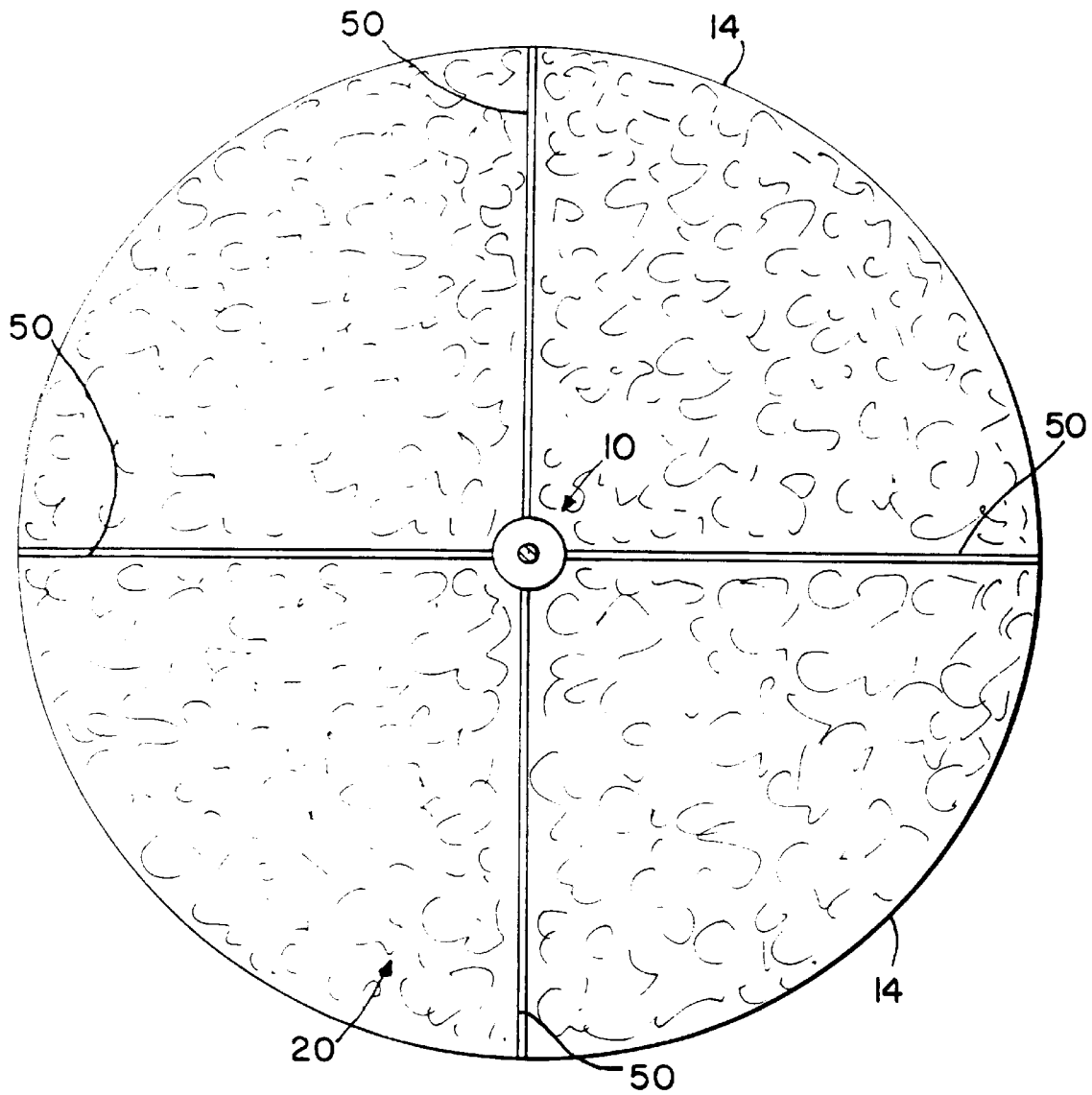
FIG. 3 is a proximal end-on view of the filter membrane shown in FIG. 2.

FIG. 3 illustrates the filter device of the invention from a distal end view in FIG. 2 with filter membrane 20 deployed. Guidewire 10 is centrally located, and structural wires 50 are seen extending from guidewire 10 to the outer edge 14 of filter membrane 20. These wires 50 provide structural integrity and rigidity to filter membrane 20. FIG. 3 depicts four, evenly-spaced structural wires 50, but there can be more or less structural wires 50. Preferably there are from two to six structural wires 50, which may be spaced regularly or irregularly. The wires 50 may preferably be comprised of stainless steel or another medically acceptable metal or alloy.

Filter membrane 20 of the invention is preferably a mesh such as that depicted in FIG. 3. The mesh should have pores of a size sufficient to block and capture any micro- and macro-emboli which may flow downstream from the site where the stenosis is being treated, but large enough such that blood flow is not impeded. The mesh used in the filter device of the invention can have a pore size of from about 20 to about 300 microns, preferably from about 50 to about 150 microns. Moreover, the size of filter membrane 20, i.e., the distance from guidewire 10 to free ends 22, is such as to allow a firm fit between filter membrane 20 and artery wall 60. The diameter of filter membrane 20 will be directly related to the artery being treated, with typical diameters ranging from about 2 mm to about 40 mm, most preferably from about 2 mm to about 20 mm.

The membrane can be comprised of fabric or non-fabric meshes, such as those used in known hemodialysis filters or heart-lung bypass machine filters. Suitable materials include polymers or physiologically acceptable metals or alloys.

Figure 4:
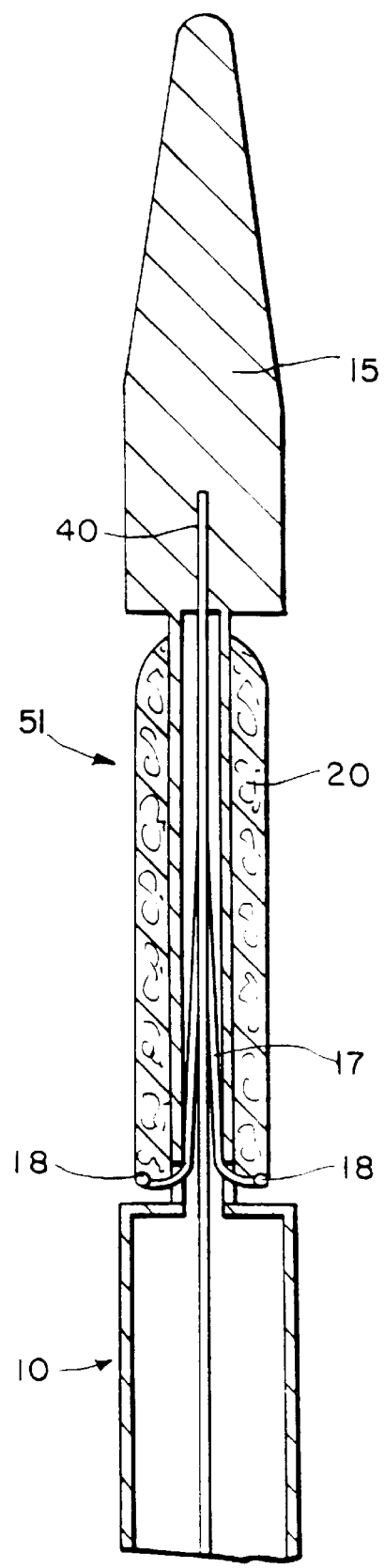
FIG. 4 is a lateral, partly cross-sectional view of another embodiment of the invention.
Figure 5A:
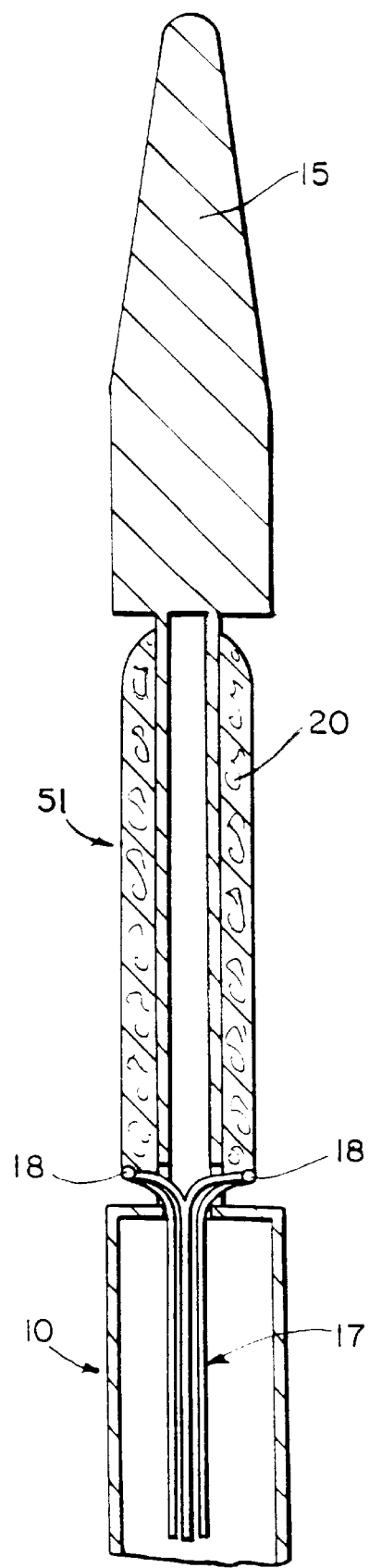
FIG. 5A is a lateral, partly cross-sectional view of a further embodiment of the invention.
Figure 5B:
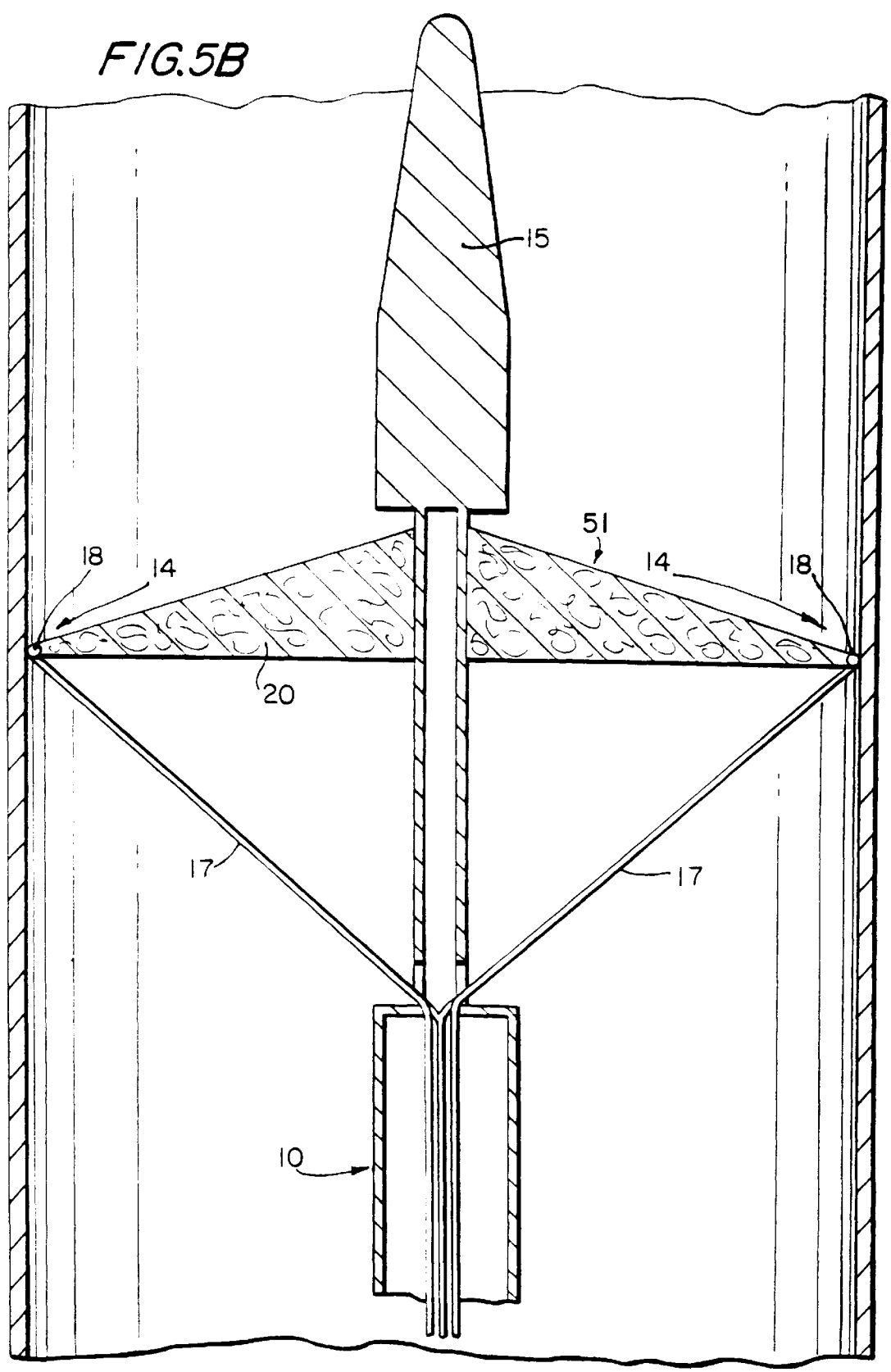
FIG. 5B is a lateral, partly cross-sectional view of the embodiment of the invention shown in FIG. 5A with the filter membrane in an expanded, deployed position.

In alternative embodiments of the invention shown in FIGS. 4, 5A and 5B, filter membrane 20 will be suspended between from two to eight, preferably from four to eight, thin metal wires 51 which serve as spines for filter membrane 20. Wires 51 may be comprised of stainless steel or another metallic alloy, nitinol, or another shape-memory material. Wires 51 will be constructed so that they assume a 90° angle with guidewire 10 when they are in an unconstrained state. This will result in expansion of the filter membrane 20 to a position normal to guidewire 10. A set of thin fibers 17 are attached at attachment points 18 to filter membrane outer edge 14 and are used to collapse filter membrane 20.

FIG. 4 shows an embodiment of this invention in which metal wires 51 are allowed to regain their 90° angle unconstrained state by use of a moveable core 40 that runs through guidewire 10. Prior to retraction of moveable core 40, fibers 17 are sufficiently tensed so as to restrain wires 51. Upon retraction of moveable core 40, tension in fibers 17 is released and wires 51 are allowed to revert to their relaxed shape, which will result in expansion of filter membrane 20 to a position normal to guidewire 10.

FIGS. 5A and 5B show an embodiment of the invention wherein wires 51 are restrained by fibers 17 that run through guidewire 10 and that are controlled at a remote location. In FIG. 5A, there is sufficient tension in fibers 17 to maintain wires 51 in a constrained position. In FIG. 5B, tension in fibers 17 has been relaxed such that wires 51 are allowed to revert to their relaxed shape, which will result in expansion of filter membrane 20 to a position normal to guidewire 10.

Figure 6:
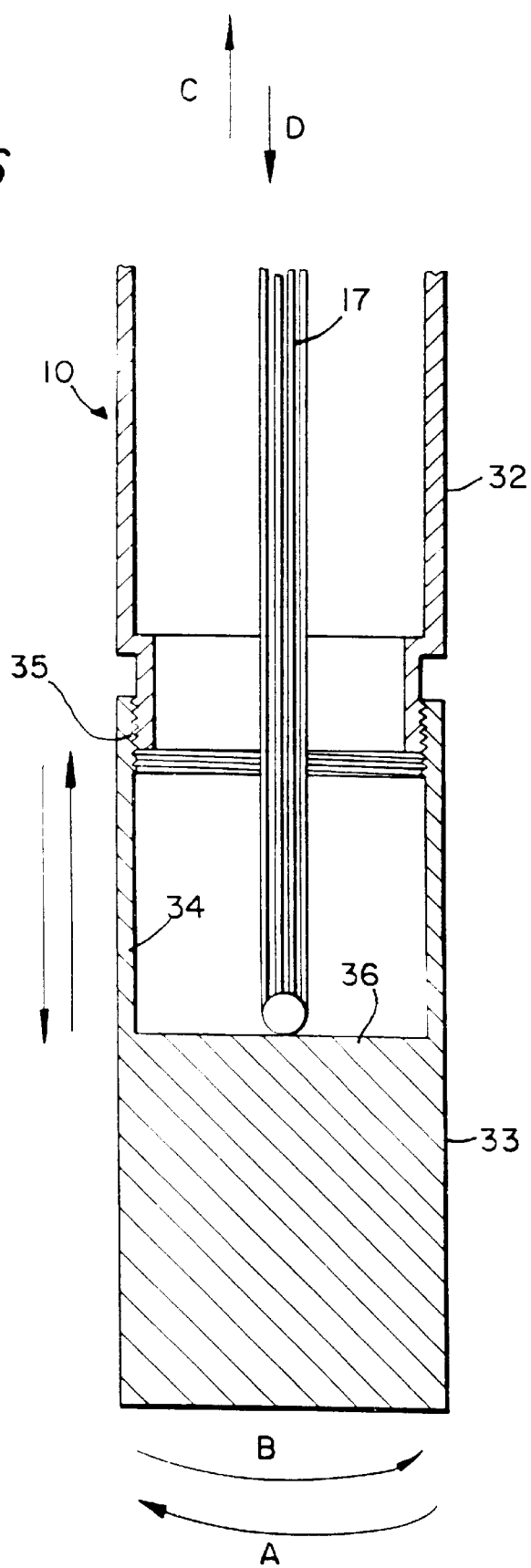
FIG. 6 is a partly cross-sectional view of a control handle for the invention.

FIG. 6 depicts a control handle especially suitable for the embodiment of the invention shown in FIGS. 5A and 5B. The proximal end 32 of guidewire 10 is rotatably attached to handle 33, such that rotation of handle 33 causes handle 33 to move distally or proximally relative to proximal guidewire end 32. For example, handle 33 may have threads 34 which engage threads 35 on guidewire proximal end 32. Fibers 17 attached to filter membrane 20 are secured in a base 36 of handle 33. Then, as handle 33 is turned, the fibers 17 move distally or proximally to open or close filter membrane 20.

As handle 33 is turned clockwise in the direction of arrow A and fibers 17 are allowed to move distally in the direction of arrow C, the tension on the filter membrane fibers 17 decreases and wires 51 are allowed to assume their natural 90° angle with respect to the guidewire, resulting in opening of filter membrane 20. Similarly, when handle 33 is turned counter-clockwise in the direction of arrow B and fibers 17 are pulled proximally in the direction of arrow D, the tension on filter fibers 17 increases, causing filter membrane 20 to collapse tightly against guidewire 10. Of course, the direction of turn of handle 33 as discussed above can be reversed, as long as threads 34,35 are properly formed to allow appropriate movement of handle 33 relative to guidewire proximal end 32.

Figure 11:
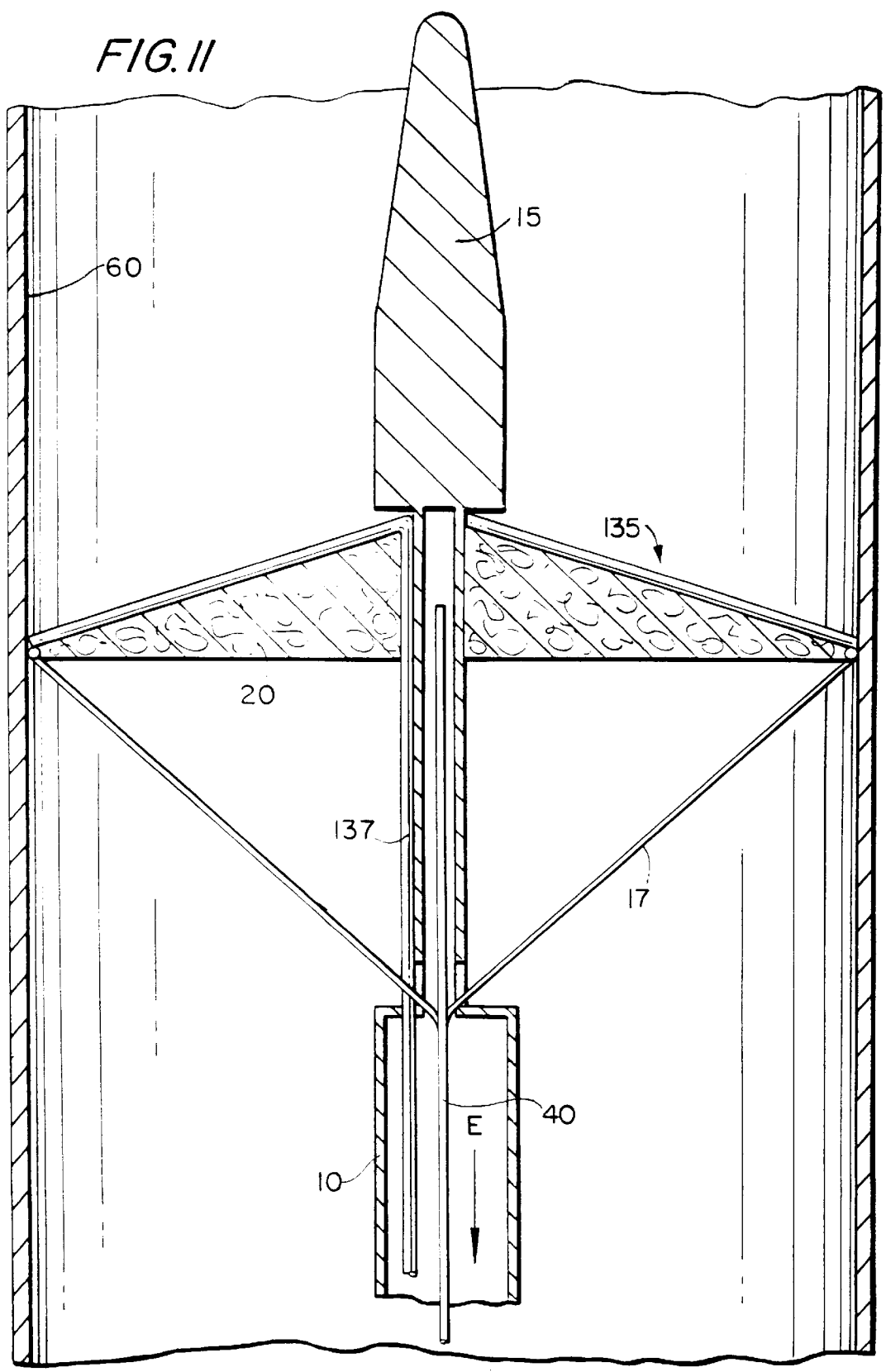
FIG. 11 is a partial cross-sectional view of another embodiment of the invention having inflatable support spines.

In yet another embodiment of the invention, shown in FIG. 11, filter membrane 20 can be supported by inflatable spines 135 supporting the filter membrane 20. Spines 135 supporting the filter membrane 20 are from two to six hollow plastic tubes which are inflatable using, for example, a standard balloon angioplasty inflation device or endoflator in fluid connection through channel 137 with spines 135. Inflation of spines 135 causes them to become rigid and deploys filter membrane 20. The underside of the filter membrane is attached to very thin fibers 17 which are attached to moveable core 40 inside hollow guidewire 10. Filter membrane 20 is collapsed by deflating the spines 135 and withdrawing the moveable core 40 in the direction of arrow E until the membrane 20 fits tightly against guidewire 10.

Figure 7:
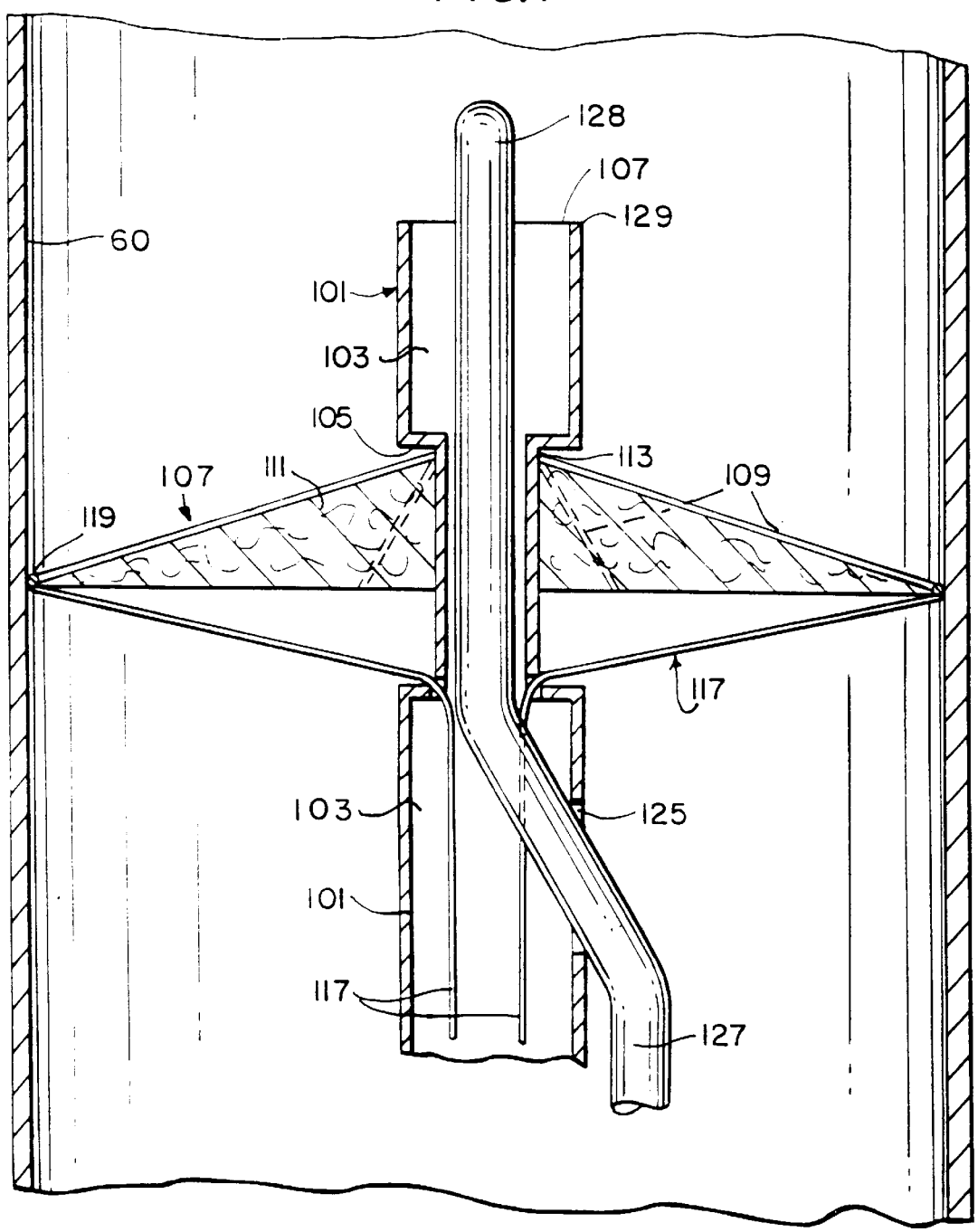
FIG. 7 is a partly cross-sectional view of another embodiment of the invention.

A catheter-based configuration is also possible, as shown in FIG. 7. In this design, the guidewire is not part of the filter catheter; the guidewire and filter catheter are two separate components. The filter catheter has an entry hole for the guidewire below the attachment of the filter membrane and the guidewire exits out the end of the filter catheter. The filter catheter could be designed to accommodate a variety of guidewire sizes, most commonly a 0.014 inch guidewire. The advantages of this design are that a variety of guidewires could be used; the lesion could be crossed with the guidewire prior to crossing with the filter catheter; the filter catheter could be removed from the artery without removing the guidewire; and the filter catheter could be made smaller.

In the embodiment of the invention shown in FIG. 7 a catheter 101 comprises a longitudinally extending lumen 103, which has an annular recess 105 adjacent the distal end of catheter 101 Positioned within recess 105 is a filter 107 comprised of structural wires 109 and a filter membrane 111. The distal end of each of wires 109 is attached at point 113 in recess 105. Fibers 117 extend from the proximal ends 119 of wires 109 proximally to a control means such as described in FIG. 6.

Catheter 101 contains guidewire port 125 located proximal to recess 105.. It is intended that in use the distal portion 128 of a guidewire 127 will be threaded into the distal end 129 of catheter 101 and out through port 125.

Alternatively, and not shown here, a catheter 101 could comprise a longitudinally extending lumen and a shorter tracking lumen that extends from distal end 129 to a point proximal to recess 105. The distal end of guidewire 127 would then be threaded into the distal opening of the tracking lumen and out the proximal end of the tracking lumen.

Figure 8:
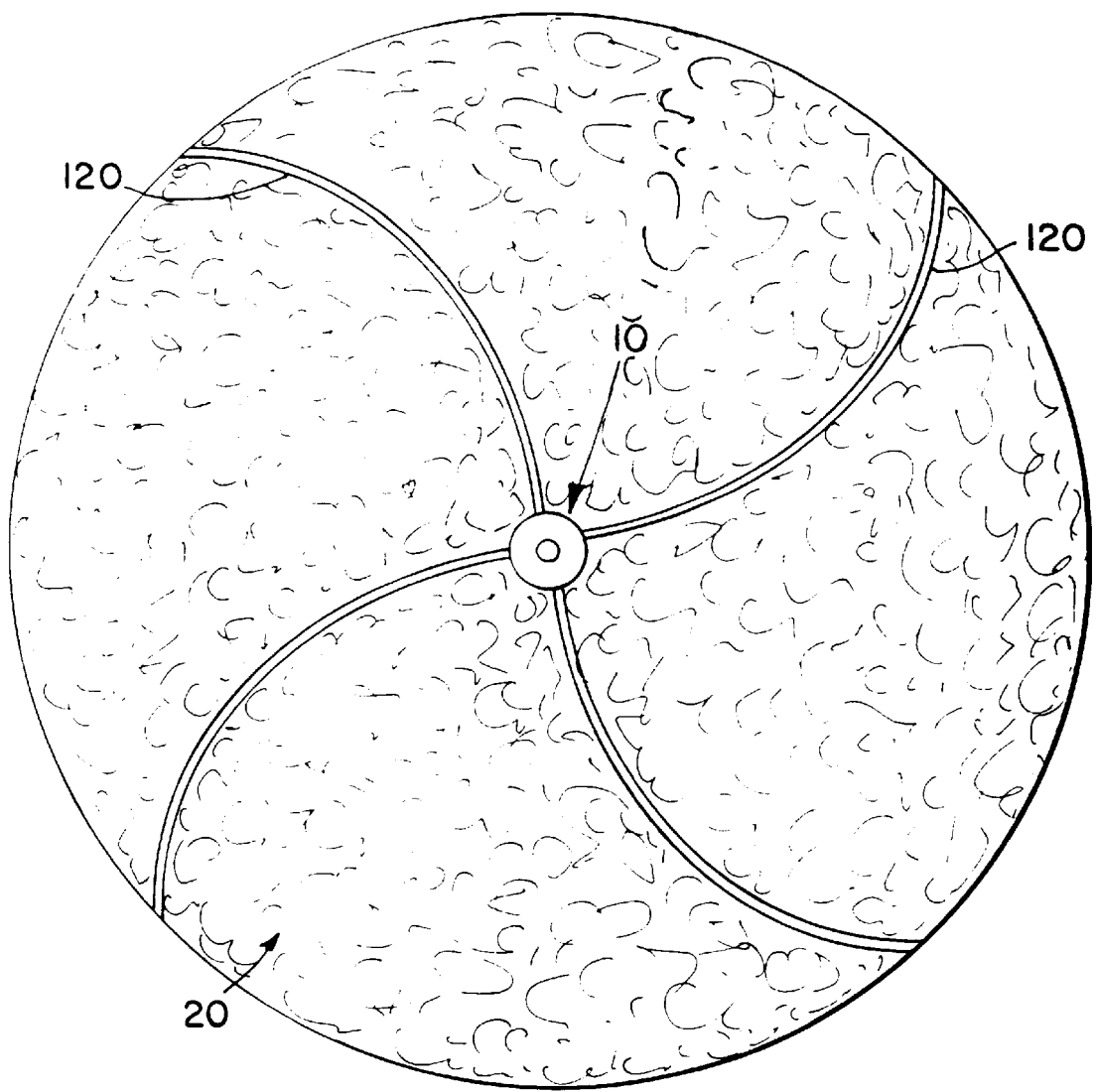
FIG. 8 is a partial cross-sectional view of an embodiment of the invention wherein the filter membrane has curved supports.

Spiral or curved structural wires may be used to deploy the filter membrane instead of straight wires. FIG. 8 illustrates the use of four curved wires 120. The angulation of the filter attachment point of wires 120 relative to their guidewire attachment has the effect of wrapping the filter fabric around the guidewire in the undeployed state. This leads to a lower profile for the undeployed filter.

Figure 9:
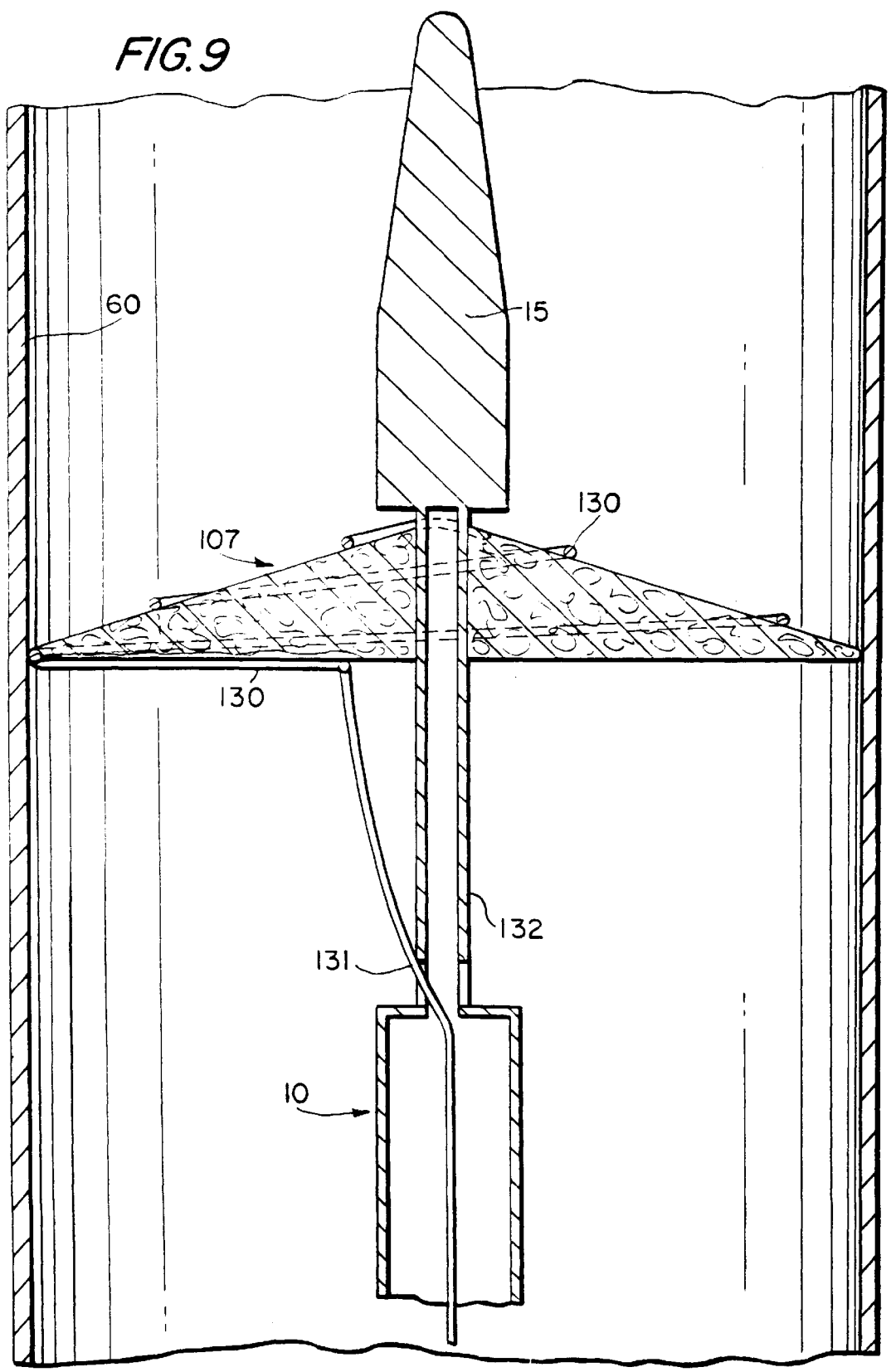
FIG. 9 is a partial cross-sectional view of yet another embodiment of the invention wherein the filter membrane has a spiral wire.
Figure 10:
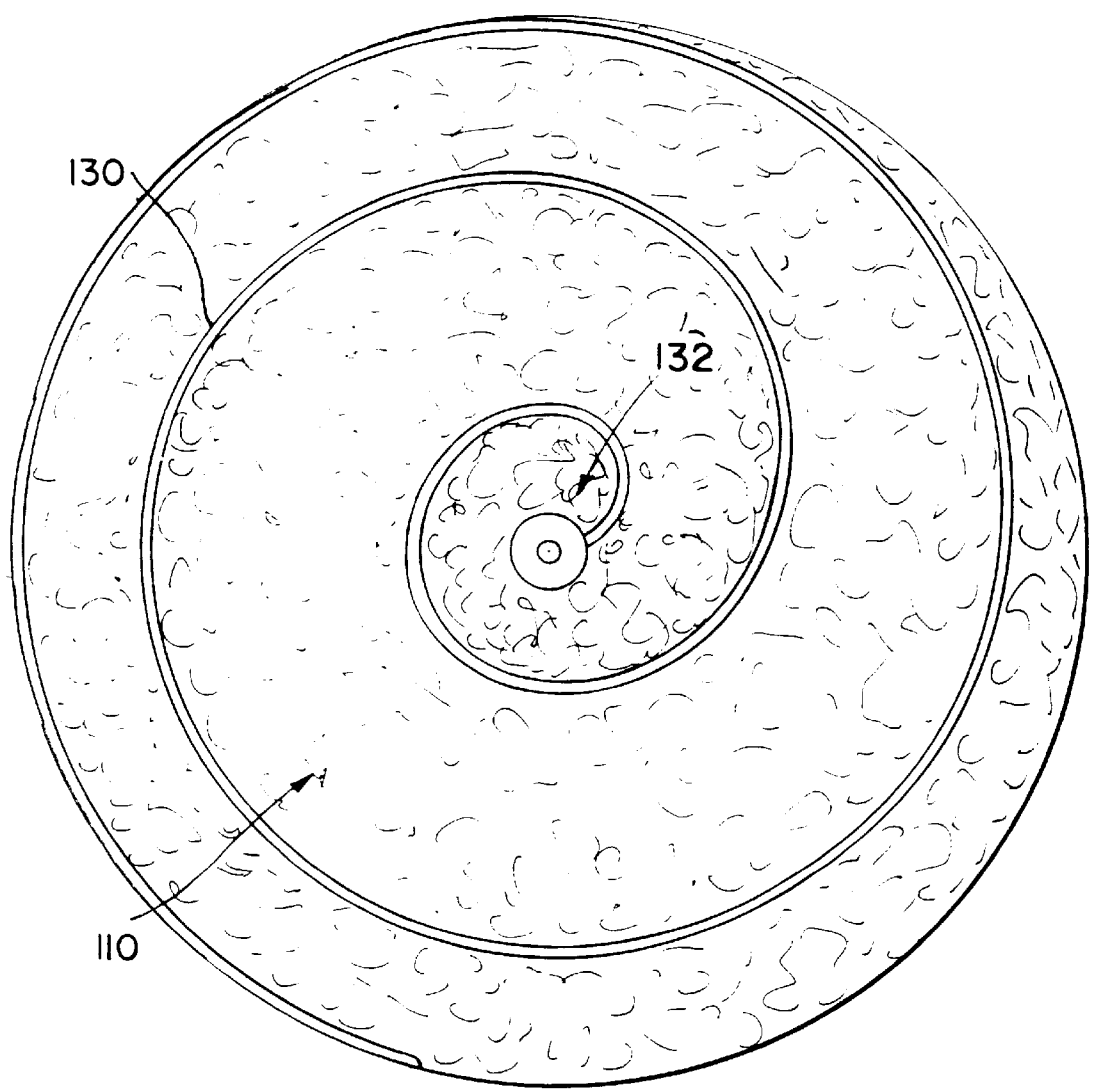
FIG. 10 is a top, cross-sectional view of the embodiment of the invention shown in FIG. 9.

FIGS. 9 and 10 illustrate the use of a single spiral structural wire 130 which is attached to the filter 107. As tension fiber 131 is released, wire 130 unwinds and deploys filter 107 in a conical configuration. This configuration has the simplicity of using a single wire and, when the tension on fiber 131 is increased, allows filter 107 to be wrapped very tightly around the guidewire shaft 131, resulting in filter 107 having a low profile in its undeployed state.

Figure 12:
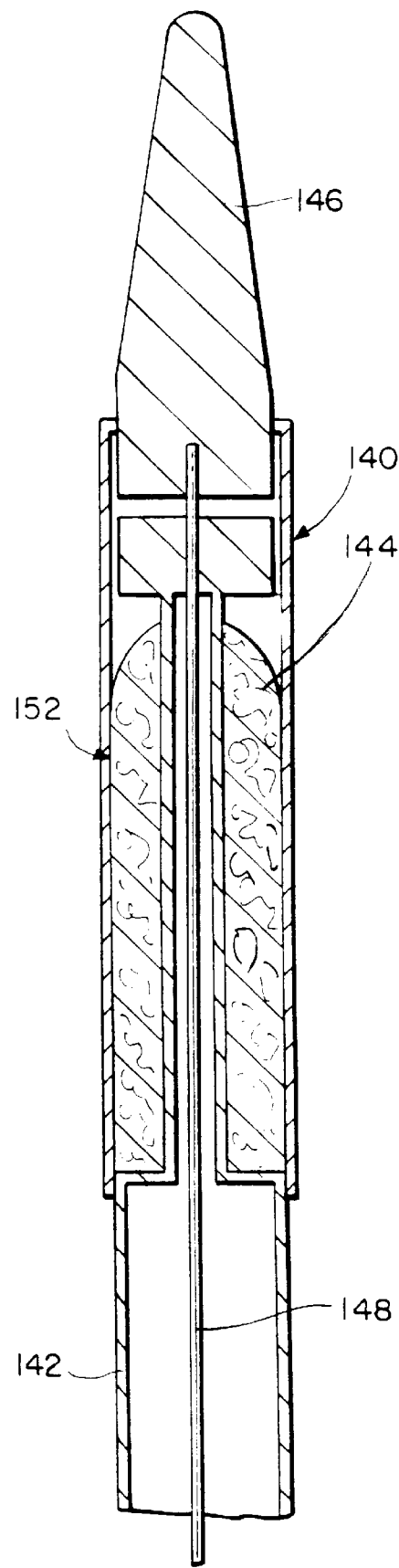
FIGS. 12 and 13 represent partial cross-sectional views of another embodiment of the invention in collapsed and deployed positions, respectively.
Figure 13:
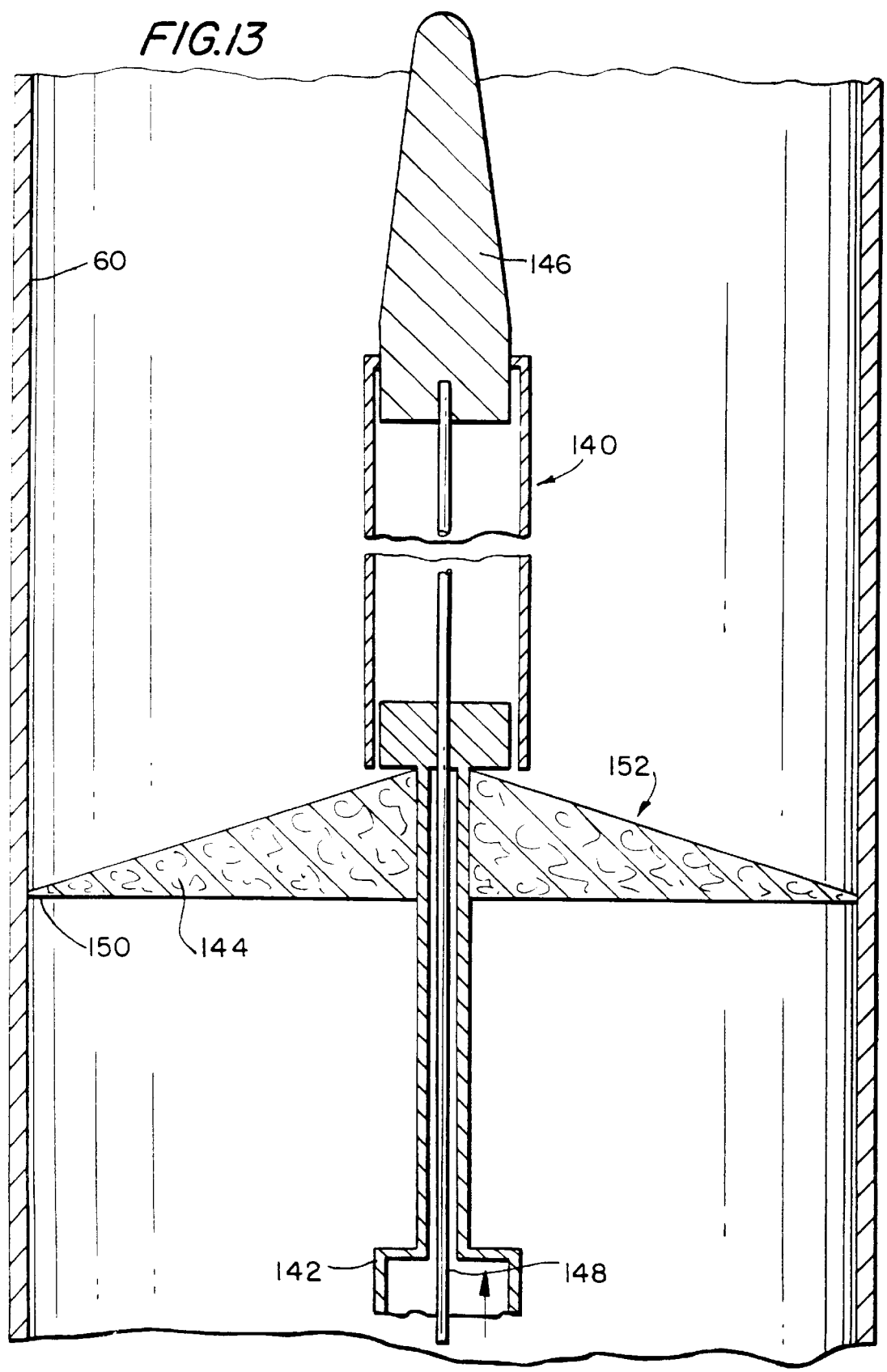

Another modification shown in FIGS. 12 and 13 comprises a retractable sheath 140 at the distal end of guidewire 142 which covers filter membrane 144 in the collapsed state. Sheath 140, the distal portion of which is affixed to guidewire tip 146, which is affixed to the distal end of moveable core 148, would prevent an edge 150 of filter membrane 144 from becoming entangled in an artery or guide catheter as it was being withdrawn from a patient.

More specifically, when guidewire 142 with tapered tip 146 is inserted percutaneously into a patient, sheath 140 covers collapsed filter membrane 144. After the filter membrane is determined by fluoroscopy to be in proper position, moveable core 148 is pushed distally to cause sheath 140 to "release" filter membrane 144, which has spines 152, to cause filter membrane 144 to deploy, as shown in FIG. 13.

FIG. 14 illustrates a lateral, cross-sectional view of a distal end of a guidewire 160 with a filter membrane 170 attached thereto. FIG. 14 shows guidewire 160 with a shapeable soft "floppy" tip 162 at its extreme distal end which provides flexibility and maneuverability to guidewire 160. The filter membrane in FIG. 14 is in an open position.

Guidewire 160 comprises a core wire 164, which extends into floppy tip 162, and a sheath 166. Filter membrane 170 is supported by a basket 169 comprising two or more filter basket wires 168, having distal ends 172 and proximal ends 174. The distal ends 172 of basket wires 168 are fixedly attached by distal radiopaque marker or crimp band 176 to core wire 164, and the proximal ends 174 of basket wires 168 are attached to proximal radiopaque marker or crimp band 178, which is slidable over core wire 164, optionally with a polymeric, such as polyimide, or metallic sleeve between core wire 164 and proximal ends 174, optionally, and preferably, proximal marker 178 is fixedly attached to core wire 164, and distal marker 176, with a polymeric or metallic sleeve, is slidable over core wire 164.

A sheath member 180 is attached to the distal end of sheath 166, sheath member 180 having a lumen 182 with a diameter and length sufficient to receive or slide over proximal marker 178. Sheath 166 and sheath member 180 can be either separate pieces bonded together or a continuous, integral structure. Sheath 166 and sheath member 180 are each made from low friction polymeric material, preferably polytetrafluoroethylene, polyethylene, nylon, or polyurethane.

Filter membrane 170 can comprise a number of different metallic or non-metallic permeable membranes having sufficient porosity to facilitate blood flow but having sufficiently small openings to capture emboli. Filter membrane 170 must be affixed at least at its distal portion 184 to core wire 164 and/or basket wire distal ends 172 and, optionally, to basket wires 168. The remainder of filter membrane 170 can be unattached or, preferably, attached to basket wires 168, such as by a suitable adhesive. Preferably basket wires 168 are encapsulated in membrane 170.

Basket 169 can be somewhat cylindrical in its middle with tapered, conical proximal and distal portions. Alternatively, basket 169 can be slightly spherical, optionally with a flat, cylindrical middle portion. Preferably basket 169 is from about 5 to about 40 mm in length and from about 2 to about 30 mm, or from about 2 to about 20 mm, in diameter at its widest.

The proximal end of sheath 180 is attached to control handle or guidewire torquer 186. Control handle 186 has an opening 188 for core wire 164 so that sheath 180 can move slidably over core wire 164. For example, when sheath 180 is moved distally toward basket wires 168, filter membrane 170 collapses. Also, there may be instances where sheath 180 will be removed proximally so that other catheters or cardiovascular appliances can be introduced over core wire 164. Control handle 186, which functions as a torque device, also primarily functions to lock sheath 180 to core wire 164 during insertion.

There are a number of known, commercially available guidewire torquers that can be modified to function as control handle 186. Modification includes, but is not limited to, providing a slightly larger central lumen.

In FIG. 15 sheath 166 and sheath member 180 are shown advanced distally so that basket wires 168 and filter member 170 are collapsed against core wire 164. The distal end 192 of sheath member 180 may optionally be slightly tapered to provide a better profile for insertion.

Figure 16:
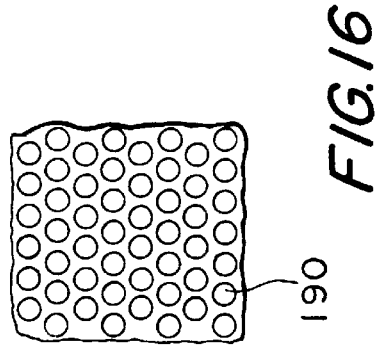
FIG. 16 is a schematic representation of a portion of a filter membrane useful according to the invention.

In a preferred embodiment of the invention, as shown in FIG. 16, filter membrane 170 comprises a polymeric material such as polyurethane or silicone elastomer that has laser-drilled holes 190. Such holes 190, a pattern for which can be seen in FIG. 16, are preferably only on the conical portion of filter membrane 170. The holes 190 could be from about 50 to 300 μm in diameter. The vertical row separation of holes 190 can be from 1.2 to 1.4 times the hole diameter and the center-to-center diameter of holes 190 can be from about 1.4 to 1.6 times the hole diameter, or in a preferred embodiment the vertical and horizontal spacing of the holes is such that the center-to-center spacing of the holes is from about 1.2 to 2.0 times the hole diameter. Preferably the open area of the holes represents from about 10 to 50 percent, more preferably from about 10 to 40%, of the filter surface.

Basket wires 168 could be comprised of a suitable, physiologically acceptable metal. Stainless steel or nitinol are preferred, although titanium or other metal alloys could be used.

Figure 17:
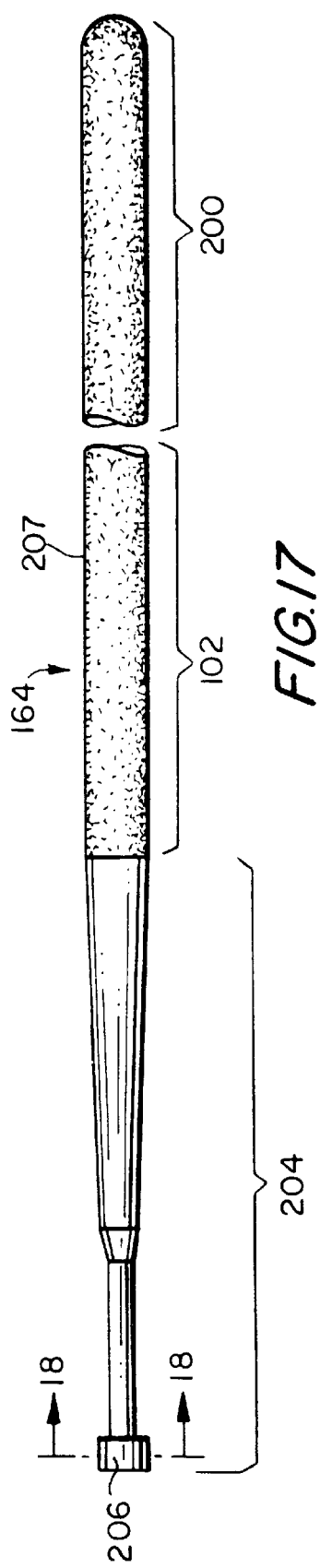
FIG. 17 is a lateral view of a core wire useful according to the invention.
Figure 18:
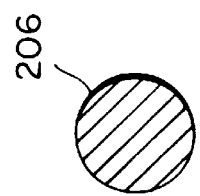
FIG. 18 is a cross-sectional view across line 18—18 of a portion of the core wire of FIG. 17.

Core wire 164 can be seen better in FIG. 17, where the proximal and middle portions 200 and 202 are substantially uniform in diameter, and then the distal portion 204 tapers to an end point 206. In fact, distal portion 204 could taper uniformly or, more preferably, non-uniformly, as shown in FIG. 17. Typically core wire 164 is from about 250 to 300 cm in length, with an initial diameter of from about 0.009 to 0.038 in., preferably from about 0.014 to 0.018 in. Distal section 204 is typically from about 8 to 10 cm. in total. With a diameter that tapers to from about 0.001 to 0.005 in. Core wire 164 may optionally have a thin polymeric coating 207 for friction reduction. Preferably end point 206 is a solid, squat cylinder, as shown in FIGS. 17 and 18.

Floppy tip 162 preferably comprises a radiopaque helical spring 210 that is fixedly attached, e.g., by welding, brazing, or soldering, to end point 206 and, optionally, attachment point 208. Optionally spring coil 210 may have a polymeric or lubricious coating 212.

FIG. 19 represents an alternate design where basket wires 220 are substantially helical in shape. Filter member 222 covers or encompasses the distal portion of basket wires 220, and the proximal and distal portions of basket wires 220 are secured by proximal radiopaque marker or crimp band 224 and distal radiopaque marker or crimp band 226, respectively. Markers 224 and 226 are fixed or slidable on core wire 228 as described above. Preferably there are from 4 to 8 basket wires 220, each with a rotation of from about 45° to 360°

Figure 21:
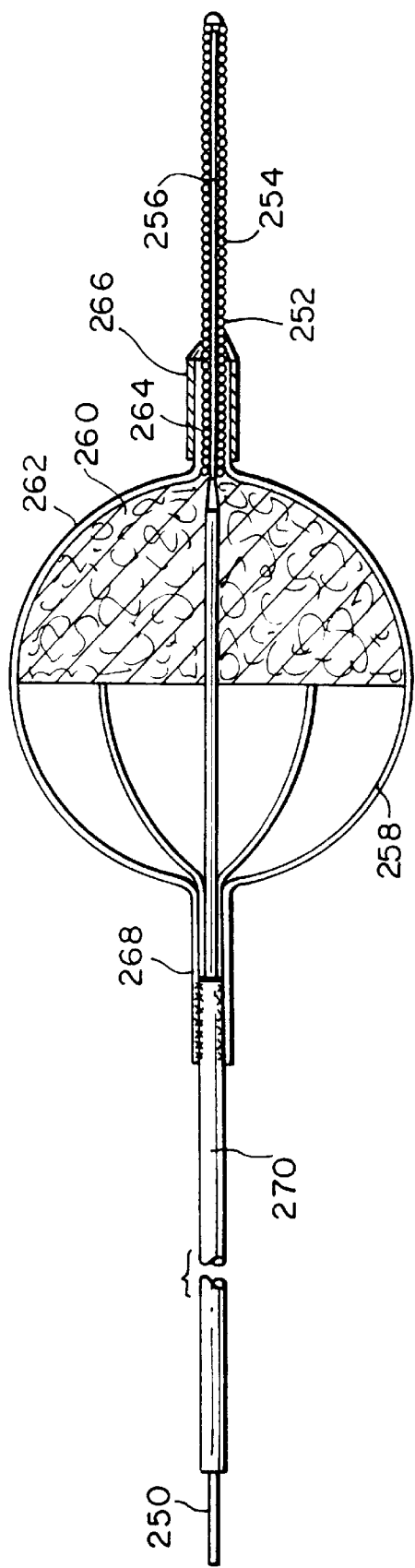
FIG. 21 is a lateral, partly cross-sectional view of a further embodiment of the invention.

Additional embodiments of the invention can be seen in FIGS. 20 and 21. The schematic representation in FIG. 20 depicts a filter membrane 280 supported by strut wires 282. The distal ends 284 of strut wires 282 are attached to the distal portion of a tubular member 286. A movable core wire 290 extends through a lumen 292 in tubular member 286 to a distal floppy section 294, where a helical spring coil 296 surrounds the distal portion 298 of core wire 290 and is attached to end point 300. There is an attachment point 302 of weld or solder at the proximal portion of spring coil 296 where the distal portion 304 of sheath member 306 is also attached to core wire 290. The lumen 308 of sheath member 306 is large enough so that as core wire 290 is pulled proximally, or tubular member 286 is advanced distally, the distal ends 284 of strut wires 282 move into lumen 308 and collapse filter membrane 280.

Moveable core wire 250 of the structure shown in FIG. 21 comprises a floppy tip 252 where a helical spring coil 254 encompasses the distal portion 256 of core wire 250. A basket wire structure component of two or more basket wires 258 supports a filter membrane 260 on the distal portion 262 of the basket structure. Distal ends 264 of the basket wires 258 are encompassed by a radiopaque marker or crimp band 266 that is attached to core wire 250 and/or spring coil 254. The proximal ends 268 of basket wires 258 are attached to the distal portion of a sheath 270 that surrounds core wire 250. Sheath 270 moves slidably over core wire 250 so that when sheath 270 is pulled proximally over core wire 250, filter membrane 260 collapses.

In FIG. 22 a basket 320 comprised of from 4 to 8 strut wires 322 is secured by a distal fixed grommet 324 and a proximal slidable grommet 326. Grommet 326 is slidable over core wire 328. Filter membrane 330 is attached to or arranged upon basket 320, with the proximal section 332 of the membrane 290 being open to flow, represented by arrows 334. The distal portion 336 of membrane 330 forms a conical shape 340 that extends proximally. The filter could be deployed by, for example, a sheath or a tube fixed to the proximal slidable crimp band 336. This design is optimized for perfusion and emboli collection. For example, as more emboli is collected, it tends to collect in outer, non-filter areas, leaving the pores open for perfusion.

Membrane 330 preferably has holes only in distal section 336/340, which holes are arranged as described above. It is believed that under normal, substantially laminar flow conditions debris or emboli 342 will tend to collect in annular recesses 344.

To close and capture emboli, as shown in FIG. 23, slidable grommet 326 is moved proximally to collapse basket 320 and membrane 336. This can be accomplished with, for example, sheath 350 or a fixed tubular member or other apparatus that is preferably slidable over the core wire.

The wires, membrane, and other materials of this embodiment are consistent with those described above.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A removable percutaneous vascular filter system for blocking micro- and macro-emboli in a vessel while allowing continued perfusion of blood, comprising:
   a guidewire having distal and proximal ends,
   a filter comprising (a) a non-metallic, porous, flexible filter membrane having a distal portion and a proximal free portion and (b) a filter membrane support structure extending from the flexible filter membrane distal portion to at least the flexible filter membrane proximal portion, wherein said filter membrane distal portion is pivotally attached to the guidewire near said distal end of the guidewire and wherein the filter membrane proximal free end portion is substantially parallel to the guidewire in its collapsed state, and deploying means operatively connected to the filter to cause the filter membrane proximal free end portion to move from a position substantially parallel to the guidewire to a position removed from the longitudinal axis of the guidewire to cause the flexible filter membrane to form a substantially conical shape to form a generally sealing relationship with the wall of said vessel.

2. The vascular filter system of claim 1, whereby the deploying means comprises a control mechanism at the proximal end of the guidewire operatively connected to the filter.

3. The vascular filter system of claim 1, wherein the pore size of the filter membrane is from about 20 to about 300 microns.

4. The vascular filter system of claim 1, wherein the deploying means comprises a moveable core, the moveable core being slidably positioned in the interior of the guidewire.

5. The vascular filter system of claim 4, wherein the deploying means further comprises deploying fibers each having first and second ends and said filter membrane further comprises an outer edge, and wherein said deploying fibers are each attached at a first end to the moveable core and are attached at a second end to the outer edge of the filter membrane.

6. The vascular filter system of claim 5 further comprising a means for collapsing the filter membrane from a deployed state to a collapsed state.

7. The vascular filter system of claim 6, wherein the collapsing means further comprises collapsing wires each having first and second ends, wherein said collapsing wires are each attached at a first end to the moveable core and are further attached at a second end to the outer edge of the filter membrane.

8. The vascular filter system of claim 7, wherein the moveable core creates a tension in the collapsing wires when it slides proximally in relation to the guidewire, and said tension causes the filter membrane to collapse tightly against the guidewire.

9. The vascular filter system of claim 3, wherein the moveable core creates a tension in the deploying fibers when it slides proximally in relation to the guidewire, and said tension causes the filter membrane to expand outwardly until the outer edge of the filter membrane is in firm contact with a lumen wall.

10. A removable percutaneous vascular filter system for blocking micro- and macro-emboli while allowing continued perfusion of blood, comprising:

a guidewire having distal and proximal portions, wherein there is a recess in the distal portion, the recess having distal and proximal ends, a filter comprising (a) a non-metallic, porous, flexible filter membrane having a distal portion and a proximal free end portion and (b) a filter membrane support structure extending from the flexible filter membrane distal portion to at least the flexible filter membrane proximal portion, wherein the flexible membrane distal portion is pivotally attached to the guidewire near the distal end of the guidewire recess and wherein the flexible membrane proximal free end portion is positioned in the recess when the filter membrane is in a collapsed state, and deploying means operatively connected to the filter to cause the filter membrane proximal free end portion to move from a position substantially parallel to the guidewire to a position removed from the longitudinal axis of the guidewire to cause the flexible filter membrane to form a substantially conical shape to form a generally sealing relationship with the wall of said vessel.

11. The vascular filter system of claim 10, wherein the deploying means is a handle or shaft that can be used to release or collapse the filter membrane.

12. The vascular filter system of claim 10, wherein the filter membrane comprises a set of inflatable spines, said spines being hollow plastic tubes.

13. The vascular filter system of claim 12 which further comprises an inflator for inflating the spines, wherein said spines become rigid upon inflation.

14. The vascular filter system of claim 13, where the inflator is an endoflator.

15. A method of treating diseased corporeal blood vessels in a patient, comprising the steps of:

(a) percutaneously inserting a removable vascular filter system comprising:

a guidewire having distal and proximal ends, a filter comprising (1) a non-metallic, porous, flexible filter membrane having a distal portion and a proximal free end portion and (b) a filter membrane support structure extending from the flexible filter membrane distal portion to at least the flexible filter membrane proximal portion, wherein said filter membrane distal portion is pivotally attached to the guidewire near said distal end of the guidewire and wherein the filter membrane proximal free end portion is substantially parallel to the guidewire in its collapsed state, and deploying means operatively connected to the filter to cause the filter membrane proximal free end portion to move from a position substantially parallel to the guidewire to a position removed from the longitudinal axis of the guidewire to cause the flexible filter membrane to form a substantially conical shape to form a generally sealing relationship with the wall of said vessel, into a diseased blood vessel to position the filter distal to a diseased segment of the vessel;

(b) deploying the filter;

(c) advancing a therapeutic catheter distally over the guidewire to the diseased segment;

(d) treating the diseased segment with the therapeutic catheter, whereby any loosened fragments from the diseased segment are carried distally by blood flow and are captured by the deployed filter;

(e) withdrawing the therapeutic catheter from the blood vessel;

(f) collapsing the filter with any trapped fragments; and (g) withdrawing the vascular filter system from the blood vessel.

16. The method of claim 15, wherein the therapeutic catheter has a stent arranged thereon or comprises a dilatation balloon.

17. The method of claim 15, wherein the therapeutic catheter comprises a surgical device.

18. A method of percutaneously capturing emboli after a surgical or interventional procedure in a patient, comprising the steps of:

(a) percutaneously inserting a removable vascular filter system comprising:
a guidewire having distal and proximal ends,
a filter comprising (1) a non-metallic, porous, flexible filter membrane having a distal portion and a proximal free end portion and (b) a filter membrane support structure extending from the flexible filter membrane distal portion to at least the flexible filter membrane proximal portion, wherein said filter membrane distal portion is pivotably attached to the guidewire near said distal end of the guidewire and wherein the filter membrane proximal free end portion is substantially parallel to the guidewire in its collapsed state, and
deploying means operatively connected to the filter to cause the filter membrane proximal free end portion to move from a position substantially parallel to the guidewire to a position removed from the longitudinal axis of the guidewire to cause the flexible filter membrane to form a substantially conical shape to form a generally sealing relationship with the wall of said vessel, into a diseased blood vessel to position the filter distal to a diseased segment of the vessel;
(b) deploying the filter;
(c) collapsing the filter with any trapped emboli; and
(d) withdrawing the guidewire from the blood vessel.

19. The method of claim 18 which comprises the additional steps after step (b) of:
advancing a therapeutic catheter distally over the guidewire to a diseased segment,
treating the diseased segment with the therapeutic catheter, whereby any loosened fragments from the diseased segment are carried distally by blood flow and are captured by the deployed filter, and withdrawing the therapeutic catheter from the blood vessel.

20. A removable percutaneous vascular filter system for blocking micro- and macro-emboli while allowing continued perfusion of blood, comprising:
a guidewire having distal and proximal ends,
a filter comprising (a) a non-metallic, porous, flexible filter membrane having a distal portion and a proximal free end portion and (b) a filter membrane support structure extending from the flexible filter membrane distal portion to at least the flexible filter membrane proximal portion, wherein said flexible filter membrane distal portion is pivotably attached to the guidewire near said distal end of the guidewire and wherein the filter membrane proximal free end portion is substantially parallel to the guidewire in its collapsed state; and
a control handle at the distal end of the guidewire, the control handle being operatively connected to the filter to cause the filter membrane proximal free end portion to move from a position substantially parallel to the guidewire to a position removed from the longitudinal axis of the guidewire to cause the flexible filter membrane to form a substantially conical shape to form a generally sealing relationship with the wall of said vessel.

21. A percutaneous vascular filter system comprising:
a guidewire having proximal and distal ends,
a filter concentrically arranged around said guidewire, said filter comprising (a) a non-metallic, porous, flexible membrane having a distal portion and a proximal free end portion and (b) a filter membrane support structure extending from the flexible filter membrane distal portion to at least the flexible membrane proximal portion, wherein the flexible membrane distal portion is pivotally attached to the guidewire adjacent its distal end and the proximal end of the filter is attached to the guidewire, and
a sheath concentrically arranged around the guidewire and having proximal and distal ends, the distal end of the sheath having a lumen of sufficient diameter to slide over the proximal portion of the filter.

22. The vascular filter system of claim 21, wherein the proximal end of the filter is slidably attached to the guidewire by a radiopaque marker or crimp band and the distal end of the filter is fixedly attached to the guidewire by a radiopaque marker or crimp band.

23. The vascular filter system of claim 21, wherein the proximal end of the filter is fixedly attached to the guidewire by a radiopaque marker or crimp band and the distal end of the filter is slidably attached to the guidewire by a radiopaque marker or crimp band.

24. The vascular filter system of claim 21, wherein the filter membrane is attached to only the distal portion of the filter membrane support structure.

25. The vascular filter system of claim 21, wherein the distal end of the guidewire comprises a floppy tip.

26. The vascular filter system of claim 21, wherein the proximal end of the sheath is attached to a handle.

27. The vascular filter system of claim 21, wherein the proximal end of the filter membrane is slidably attached to the guidewire by a grommet.

28. A percutaneous vascular filter system comprising:
a guidewire having proximal and distal ends, and
a filter comprising (a) a non-metallic, porous, flexible filter membrane having a distal portion and a proximal free end portion and (b) a filter membrane support structure extending from the flexible filter membrane distal portion to at least the flexible filter membrane proximal portion, the filter concentrically arranged around said guidewire, the distal end of the filter being attached to the guidewire adjacent its distal end and the proximal end of the filter being attached to the guidewire.

29. The vascular filter system of claim 28 which also comprises a sheath concentrically arranged around the guidewire and having proximal and distal ends, the distal end of the sheath having a lumen of sufficient diameter to slide over the proximal portion of the filter.

30. The vascular filter system of claim 28, wherein the filter membrane is attached to only the distal portion of the wire structure.

31. The vascular filter system of claim 28, wherein the proximal end of the filter is fixedly attached to the guidewire by a radiopaque marker or crimp band and the distal end of the filter is slidably attached to the guidewire by a radiopaque marker or crimp band.

32. The vascular filter system of claim 28, wherein the proximal end of the filter is slidably attached to the guidewire by a radiopaque marker or crimp band and the distal end of the filter is fixedly attached to the guidewire by a radiopaque marker or crimp band.

33. The vascular filter system of claim 32, wherein the distal end of the filter is inverted proximally.

34. The vascular filter system of claim 33, which also comprises a member slidable over the guidewire to collapse the filter to trap debris or emboli.

* * * * *